United States Patent [19]
Porzilli

[11] Patent Number: 5,158,555
[45] Date of Patent: Oct. 27, 1992

[54] HEAL FAST WOUND PROTECTION SYSTEM WITH PERFORATIONS

[76] Inventor: Louis B. Porzilli, P.O. Box 374, Rockaway, N.J. 07866

[21] Appl. No.: 465,968

[22] Filed: Apr. 6, 1990

[51] Int. Cl.⁵ .............................................. A61F 13/02
[52] U.S. Cl. ................................... 604/307; 604/304; 602/47; 602/59
[58] Field of Search ..................... 128/155, 156, 888; 604/304, 307, 308; 602/47, 59

[56] References Cited

U.S. PATENT DOCUMENTS

| | | | |
|---|---|---|---|
| 974,294 | 11/1910 | Pond. | |
| 1,920,808 | 8/1933 | Sander | 604/307 |
| 3,428,043 | 2/1969 | Shepherd | 128/268 |
| 3,687,136 | 8/1972 | Carmody | 128/156 |
| 3,875,937 | 4/1975 | Schmitt et al. | 128/155 |
| 4,649,909 | 3/1987 | Thompson | 128/155 |
| 4,875,473 | 10/1989 | Alvarez | 128/155 |
| 4,884,563 | 12/1989 | Sessions | 128/155 |
| 4,972,829 | 11/1990 | Knerr | 128/155 |
| 5,056,510 | 10/1991 | Gilman | 128/155 |

Primary Examiner—Paul Prebilic
Attorney, Agent, or Firm—Sheldon H. Parker

[57] ABSTRACT

A protective dressing consisting of a two sided plastic strip, with a first, a second and a third portion. The second portion has a removably affixed perforated cover on one side and a gauze layer, a thick absorbent pad and a non-stick layer on the other side. The perforated cover can be removed and reaffixed to allow for increased or decreased oxygenation.

19 Claims, 1 Drawing Sheet

HEAL FAST WOUND PROTECTION SYSTEM WITH PERFORATIONS

BACKGROUND OF THE INVENTION

1. Field of the Invention

This invention relates to a multilayer dressing which allows for increased ventilation. The removal of the top dressing increases the rate of oxygenation, improving the rate of epidermal healing.

2. Description of the Prior Art

U.S. Pat. No. 209,560, issued to Griffith relates to an improved method of plaster type bandages. Another plaster type bandage is disclosed in Sander's U.S. Pat. No. 1,920,808. An improved surgical bandage is disclosed in U.S. Pat. No. 974,294 utilizing woven fabric and gelatin-glycerin compound. Shepherd, U.S. Pat. No. 3,428,043 discloses a hydrophilic hydrogel material reinforced with a coextensive sheet of fabric. U.S. Pat. No. 4,884,563 discloses an improved bandage which has a non-stretchable, yet flexible, plastic cover sheet. In U.S. Pat. No. 3,687,136, a bandage is disclosed which allows the user to match their skin color. U.S. Pat. No. 3,875,937 to Schmitt discloses a wound dressing treated with a polyhydroxyacetic ester which becomes embedded in a wound and is later replaced by living tissue.

In Alvarez, U.S. Pat. No. 4,875,473, a multi-layer wound dressing is providing which facilitates healing using hypoxia followed by an aerobic environment. The Alvarez patent does not allow for monitoring of the wound nor is it provide for moisture to be drawing away from the wound.

The Thompson patent, U.S. Pat. No. 4,649,909, the emphasis is drawing moisture away from the wound. The primary dressing component 13 is secured to the skin of a patient. The absorbent material 12 is removably placed over the primary dressing and can be changed, as needed, without removal of the primary dressing component 13. The layers of the bandage are held in place by the fibrous backing 10. The although removable for changing, the Thompson patent does not allow for oxygenation.

Although the dressings shown in these references offer some advantages, they have not been totally successful in providing the needed ventilation which increases the epidermal healing.

SUMMARY OF THE INVENTION

A protective dressing having a plastic strip, with a removably affixed perforated cover. A mesh layer, thick absorbent pad and non-stick layer are in contact with the non-stick adhesive plastic strip, opposite the perforated cover. The plastic strip, absorbent pad and non-stick layer are perforated to allow for air flow.

BRIEF DESCRIPTION OF THE DRAWING

The specification and disclosed invention will be better understood when read in reference to the drawings in which.

DETAILED DESCRIPTION OF THE EMBODIMENT

Figure 1:
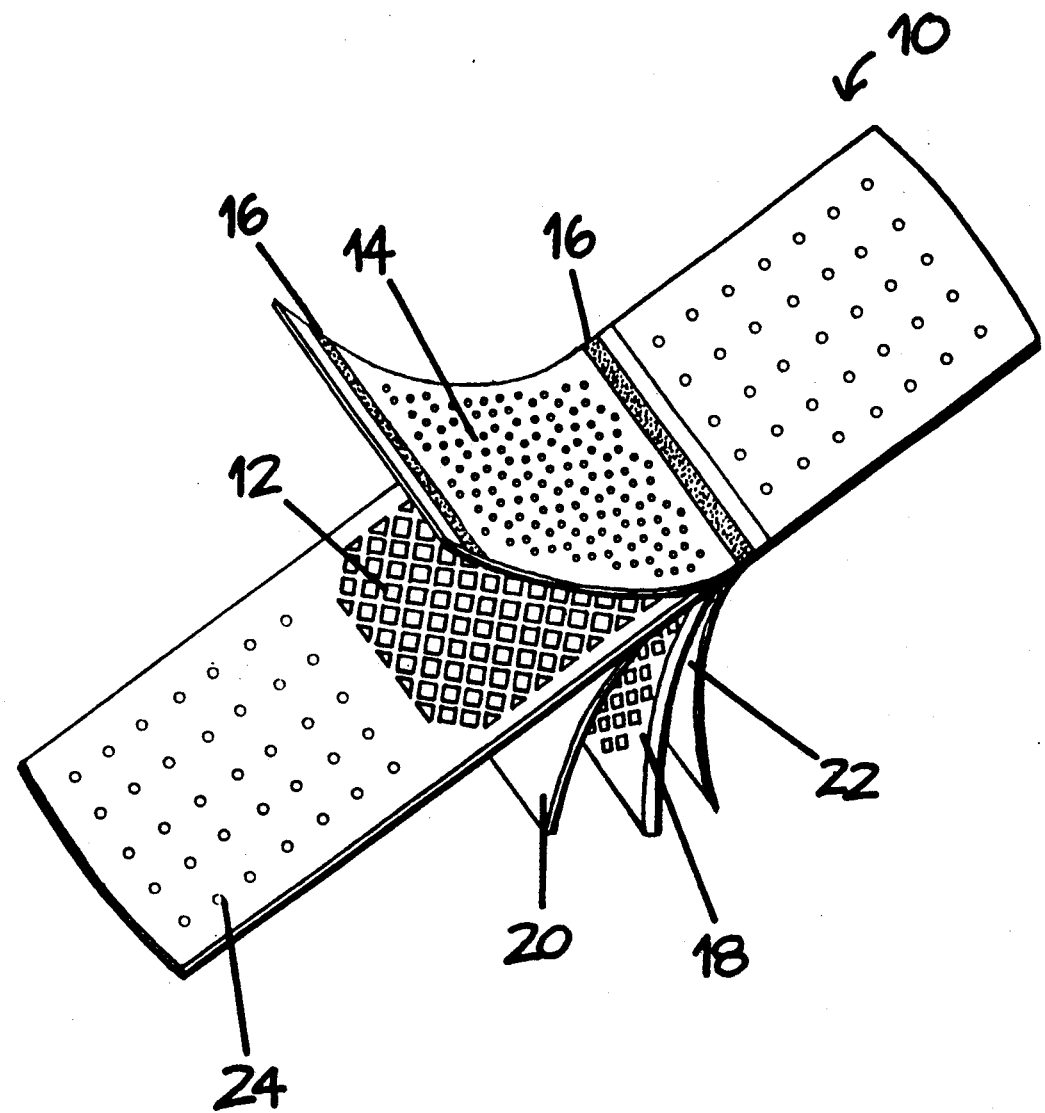
FIG. 1 is a perspective view of the device of the instant invention.

In FIG. 1 the assembled protective dressing or bandage 10 is illustrated with the separate sections pulled away from the main bandage 10 for ease of description. The plastic strip 24 is a single strip of non adhesive plastic which has been covered with a skin release adhesive, as known in the prior art. In the preferred embodiment, the non stick adhesive plastic strip 24 would be manufactured in a biodegradable plastic. The macro ventilation perforations 12 are cut into the non stick adhesive plastic strip 24 at time of manufacture. The macro ventilation perforations 12 allow for added ventilation for the wound to assist in improved epitheliazation. The macro ventilation perforations 12 as shown in FIG. 1 are cut in diamonds. It should be noted, however, that this is only one configuration which the perforations can take and any pattern can be used, providing they do not endanger the integrity of the bandage 10.

The tear perforated cover 14 is removably placed over the macro ventilation perforations 12 to provide wound closure with minimal ventilation. The perforated cover 14 is, in a preferred embodiment, manufactured from a translucent biodegradable material. Other materials can be substituted providing they provide the same benefits and meet the same medical standards which are required. The perforated cover 14 is provided with adhesive strips 16 which affix the perforated cover 14 to the non stick plastic strip 24. The adhesive strips 16, as illustrated herein, are placed at opposite ends of the perforated cover 14, however they strips 16 can be placed on all four sides, or edges, of the perforated cover 14. The adhesive strips 16 should be a material which retains its adhesive qualities to allow the perforated cover 14 to be removed and then readhered to the plastic strip 24.

The removability of the tear perforated cover 14 allow for additional oxygenation allowing for additional epitheliazation. A recent study of burn victims that there was an improved rate of epidermal healing when treated in a hyperbaric chamber. The instant invention takes advantage of the increased rate of epidermal healing through added oxygenation by allowing increased ventilation upon removal of the tear perforated cover 14.

The gauze layer 20 is placed adjacent the non stick adhesive plastic strip 24 to provide protection against macro foreign particles once the tear perforated cover 14 is removed. The gauze layer 20 is manufactured from multiple layers of gauze or synthetic mesh as well known in the prior art. The gauze layer 20 is placed directly adjacent the macro ventilation perforations 12. The term gauze is used herein to indicate "1. A very thin, light, loosely woven material, usually of silk or cotton: also applied to other material of similar open texture; as wire gauze. *Webster's New Twentieth Century Dictionary*, Second Edition. New World Dictionaries/-Simon and Schuster, New York, N.Y., 1983.

The absorbent perforated pad 18 is placed adjacent the gauze layer. The absorbent perforated pad 18 is manufactured from a thick absorbent material which will draw moisture from the wound. Medication can be added to the absorbent perforated pad 18 and is dependent upon the manufacturer. In a liquid form the medication can contain, as examples, any one of or a combination of elastin, Epidermal Growth Factor, Aloe and/or Vitamin E. A heat sensitive melting gel can be applied to the pad for release in contact with the skin. The foregoing examples are provided as examples only and any versed in the prior art will be knowledgeable in additional medications to be used in combination with the instant disclosure. The absorbent perforated pad 18 is shown with diamond cuts, however, as previously noted above, the configuration illustrated is for convenience only and other shaped cuts can be used.

A non-stick transparent material 22 is placed over the absorbent perforated pad 18 to prevent the absorbent perforated pad 18 from sticking to the wound. The non-stick transparent material 22 can be placed over the absorbent perforated pad 18 and secured to the non-stick plastic strip 24 at the time the absorbent perforated pad 18 and the gauze layer 20 are secured to the non-stick plastic strip 24. As an alternative, the non-stick transparent material 22 can be wrapped around the absorbent perforated pad 18 and gauze layer 20 and secured to the non-stick plastic strip 24 as a unit. Another alternative would be to secure the non-stick transparent material 22 directly to the absorbent perforated pad 18, covering the pad either fully or partially. The non-stick transparent material 22 must be air permeable and would generally be a perforated clear material known in the prior art.

It is critical that the gauze layer 20, absorbent perforated pad 18 and the non-stick transparent material 22 be placed directly adjacent to and lined up with the macro ventilation perforations 12, in the non-stick adhesive plastic strip 24. The perforated cover 14 must also be adjacent to and lined up with the macro ventilation perforations 12 on the opposite side of the adhesive plastic strip 24. The nonalignment of the layers inhibits the oxygenation of the wound and the increased epitheliazation.

What is claimed is:

1. A protective dressing having a plastic strip, said plastic strip having a first side and a second side, and being divided into a first, a second and a third portion, wherein
   A. said second portion of said first side of said plastic strip has a removably affixed perforated cover, said perforated cover having at least four edges and said perforations providing for ventilation;
   B. said second portion of said second side of said plastic strip having a gauze layer, said gauze layer positioned to be in contact with said plastic strip;
   C. an absorbent pad adjacent to said gauze layer;
   D. a non-stick layer adjacent to said absorbent pad;
   wherein said second portion of said plastic strip, said absorbent pad and said non-stick layer are perforated to allow for air flow, said perforations being of sufficient size to provide for ventilation.

2. The protective dressing of claim 1 wherein said plastic strip has skin releasable adhesive on said first portion and said third portion of its second side.

3. The protective dressing of claim 1 wherein said removably affixed perforated cover is translucent, whereby said wound is monitored through said translucent perforated cover.

4. The protective dressing of claim 1 wherein said removably affixed perforated cover is formed of a biodegradable material.

5. The protective dressing of claim 1 wherein said removably affixed perforated cover has surface areas proximate at least two of its four edges, said surface areas containing releasable adhesive.

6. The protective dressing of claim 1 wherein said removably affixed perforated cover can be reaffixed to said plastic strip.

7. The protective dressing of claim 1 wherein said gauze layer is a synthetic material.

8. The protective dressing of claim 1 wherein said absorbent pad further includes medication.

9. The protective dressing of claim 1 wherein said non-stick layer covers at least a portion of said gauze layer.

10. The protective dressing of claim 1 wherein said perforations in said absorbent pad, said plastic strip and said non-stick layer are sized to allow air flow through said said absorbent pad, plastic strip and non-stick layer.

11. The method of increasing epitheliazation of a wound through increased oxygenation comprising, providing a protective dressing consisting of:
    A. a protective dressing having a plastic strip, said plastic strip having a first side and a second side, and being divided into a first, a second and a third portion, wherein said second portion of said plastic strip is perforated;
    B. said second portion of said first side of said plastic strip has a removably affixed perforated cover, said perforated cover having at least four sides;
    C. said second portion of said second side of said nonstick adhesive plastic strip has a gauze layer, said gauze layer positioned to be in contact with said plastic strip;
    D. an absorbent pad adjacent to said gauze layer, said absorbent pad being perforated to allow for air flow;
    E. a non-stick layer adjacent to said absorbent pad, said absorbent pad being perforated to allow for air flow;
    applying said protective dressing to said wound,
    regulating and monitoring air flow by removing said removably affixed perforated cover to allow for increased oxygenation and reaffixing said perforated cover to decrease oxygenation.

12. The method of increasing epitheliazation of a wound of claim 11 wherein said plastic strip has skin release adhesive on said first portion and said third portion of its second side.

13. The method of increasing epitheliazation of a wound of claim 11 wherein said removably affixed perforated cover is translucent, whereby said wound is monitored through said translucent perforated cover.

14. The method of increasing epitheliazation of a wound of claim 11 wherein said removably affixed perforated cover is formed from a biodegradable material.

15. The method of increasing epitheliazation of a wound of claim 11 wherein said removably affixed perforated cover has surface areas proximate at least two of its four edges, said surface areas containing releasable adhesive.

16. The method of increasing epitheliazation of a wound of claim 11 wherein said absorbent pad further includes medication.

17. The method of increasing epitheliazation of a wound of claim 11 wherein wherein said absorbent pad absorbs moisture away from the wound.

18. The method of increasing epitheliazation of a wound of claim 11 wherein said non-stick layer covers at least a portion of said gauze layer.

19. The method of increasing epitheliazation of a wound of claim 11 wherein said perforations in said absorbent pad, said plastic strip and said non-stick layer are sized to allow air flow through said said absorbent pad, plastic strip and non-stick layer.

* * * * *